US008897953B2

(12) United States Patent
Olsen, III et al.

(10) Patent No.: US 8,897,953 B2
(45) Date of Patent: Nov. 25, 2014

(54) SYSTEMS AND METHODS FOR MANAGING FAULT CODES

(75) Inventors: John A. Olsen, III, Cumming, GA (US); David L. Bradley, Alpharetta, GA (US); Matthew S. Hendrix, Jupiter, FL (US)

(73) Assignee: United Parcel Service of America, Inc.

( * ) Notice: Subject to any disclaimer, the term of this patent is extended or adjusted under 35 U.S.C. 154(b) by 0 days.

(21) Appl. No.: 13/558,425

(22) Filed: Jul. 26, 2012

(65) Prior Publication Data

US 2013/0030641 A1    Jan. 31, 2013

Related U.S. Application Data

(60) Provisional application No. 61/511,660, filed on Jul. 26, 2011.

(51) Int. Cl.
| G01M 17/00 | (2006.01) |
| G07C 5/08 | (2006.01) |
| G05B 23/02 | (2006.01) |
| G01M 15/05 | (2006.01) |
| G07C 5/00 | (2006.01) |
| B64F 5/00 | (2006.01) |

(52) U.S. Cl.
CPC ............. G07C 5/0808 (2013.01); G01M 15/05 (2013.01); G07C 5/085 (2013.01); G07C 5/008 (2013.01); B64F 5/0045 (2013.01); G05B 23/0283 (2013.01)
USPC ........ 701/31.6; 701/29.6; 701/29.7; 701/29.9

(58) Field of Classification Search
CPC ...... G07C 5/008; G07C 5/0808; G07C 5/085; B64F 5/0045; G01M 15/05
USPC ........... 701/31.6, 29.9, 29.6, 31.4, 30.2, 29.8, 701/29.4, 99; 705/26.3, 26.4, 347; 706/12, 706/52; 123/479; 340/10.41
See application file for complete search history.

(56) References Cited

U.S. PATENT DOCUMENTS

| 3,526,127 A | 9/1970 | Sarkis |
| 4,773,011 A | 9/1988 | VanHoose |

(Continued)

OTHER PUBLICATIONS

Staff, "Oil Lasts Longer in Diesels, Thanks to Novel Viscosity Sensor," MachineDesign.com, Dec. 14, 2006, pp. 1-3, <http://machinedesign.com/article/oil-lasts-longer-in-diesels-thanks-to-novel-viscosity-sensor-1214>.

(Continued)

Primary Examiner — Behrang Badii
(74) Attorney, Agent, or Firm — Alston & Bird LLP

(57) ABSTRACT

Various embodiments of the present invention provide systems and methods for managing fault codes triggered by one or more vehicles during operation. In general, various embodiments of the invention involve recording and analyzing fault codes triggered during a particular time period while a vehicle is in operation. As a result of the analysis, various embodiments of the invention may set a state for each of the identified fault codes, the state indicating a level of action to address the identified fault code. In particular embodiments, the states may be one of a caution state indicating one or more components or sub-systems of the vehicle should be monitored, a critical state indicating one or more components or sub-systems of the vehicle should be repaired, or an environmental state indicating failure or potential failure of one or more components or sub-systems of the vehicle may affect one or more environmental conditions.

24 Claims, 8 Drawing Sheets

(56) References Cited

U.S. PATENT DOCUMENTS

Figure 1:
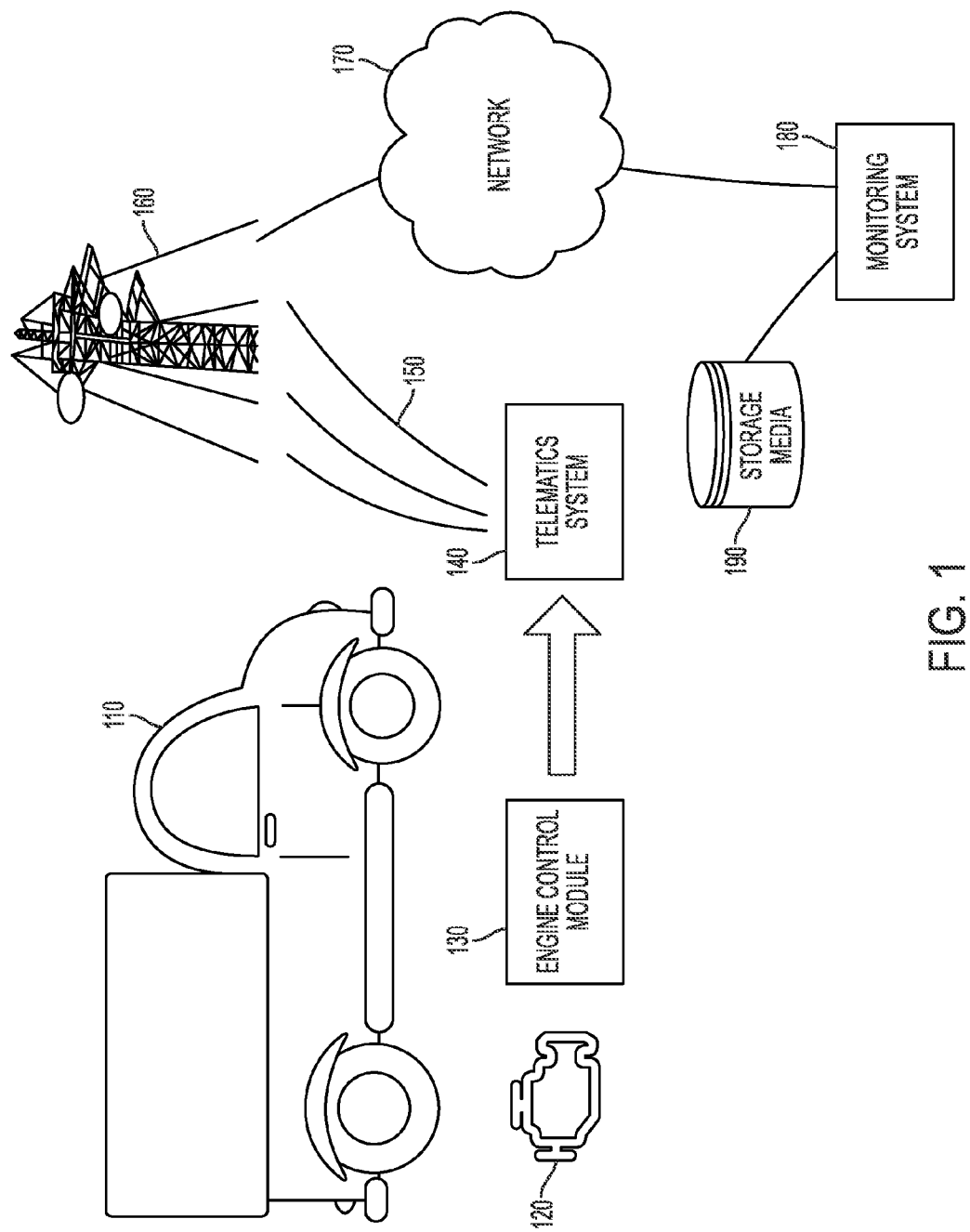

| | | |
|---|---|---|
| 4,809,540 A | 3/1989 | Lackner et al. |
| 4,945,759 A | 8/1990 | Krofchalk et al. |
| 5,041,976 A | 8/1991 | Marko et al. |
| 5,060,156 A | 10/1991 | Vajgart et al. |
| 5,491,631 A * | 2/1996 | Shirane et al. ............... 701/29.6 |
| 5,815,093 A | 9/1998 | Kikinis |
| 5,928,291 A | 7/1999 | Jenkins et al. |
| 6,084,870 A | 7/2000 | Wooten et al. |
| 6,091,325 A | 7/2000 | Zur et al. |
| 6,092,021 A | 7/2000 | Ehlbeck et al. |
| 6,112,152 A | 8/2000 | Tuttle |
| 6,181,994 B1 | 1/2001 | Colson et al. |
| 6,253,129 B1 | 6/2001 | Jenkins et al. |
| 6,301,531 B1 | 10/2001 | Pierro et al. |
| 6,306,063 B1 | 10/2001 | Horgan et al. |
| 6,324,659 B1 | 11/2001 | Pierro |
| 6,330,499 B1 | 12/2001 | Chou et al. |
| 6,338,152 B1 | 1/2002 | Fera et al. |
| 6,389,337 B1 | 5/2002 | Kolls |
| 6,424,157 B1 | 7/2002 | Gollomp et al. |
| 6,438,471 B1 | 8/2002 | Katagishi et al. |
| 6,459,969 B1 | 10/2002 | Bates et al. |
| 6,462,675 B1 | 10/2002 | Humphrey et al. |
| 6,484,080 B2 | 11/2002 | Breed |
| 6,498,986 B1 | 12/2002 | Kurtzberg et al. |
| 6,509,749 B1 | 1/2003 | Buelna et al. |
| 6,525,672 B2 | 2/2003 | Chainer et al. |
| 6,549,833 B2 | 4/2003 | Katagishi et al. |
| 6,553,816 B1 | 4/2003 | Palanisamy et al. |
| 6,594,579 B1 | 7/2003 | Lowrey et al. |
| 6,604,033 B1 | 8/2003 | Banet et al. |
| 6,609,051 B2 | 8/2003 | Fiechter et al. |
| 6,611,740 B2 | 8/2003 | Lowrey et al. |
| 6,636,790 B1 | 10/2003 | Lightner et al. |
| 6,651,034 B1 | 11/2003 | Hedlund et al. |
| 6,662,091 B2 | 12/2003 | Wilson et al. |
| 6,675,635 B2 | 1/2004 | Kasen et al. |
| 6,732,031 B1 | 5/2004 | Lightner et al. |
| 6,732,063 B2 | 5/2004 | Famili et al. |
| 6,735,504 B2 | 5/2004 | Katagishi et al. |
| 6,735,506 B2 | 5/2004 | Breed et al. |
| 6,738,697 B2 | 5/2004 | Breed |
| 6,741,938 B2 | 5/2004 | Berndorfer |
| 6,775,642 B2 | 8/2004 | Remboski et al. |
| 6,819,988 B2 | 11/2004 | Dietz et al. |
| 6,840,093 B2 | 1/2005 | Kasen et al. |
| 6,847,871 B2 | 1/2005 | Malik et al. |
| 6,850,824 B2 | 2/2005 | Breed |
| 6,857,262 B2 | 2/2005 | Rendahl et al. |
| 6,859,039 B2 | 2/2005 | Horie et al. |
| 6,911,830 B2 | 6/2005 | Heremans et al. |
| 6,920,779 B2 | 7/2005 | Carlstrom et al. |
| 6,947,827 B2 | 9/2005 | Fuse et al. |
| 6,988,026 B2 | 1/2006 | Breed et al. |
| 7,016,774 B2 | 3/2006 | Barber et al. |
| 7,050,897 B2 | 5/2006 | Breed et al. |
| 7,075,421 B1 | 7/2006 | Tuttle |
| 7,082,359 B2 | 7/2006 | Breed |
| 7,089,099 B2 | 8/2006 | Shostak et al. |
| 7,089,784 B2 | 8/2006 | Jakoby et al. |
| 7,103,460 B1 | 9/2006 | Breed |
| 7,133,804 B2 | 11/2006 | Tonack et al. |
| 7,146,264 B2 | 12/2006 | Bates et al. |
| 7,155,321 B2 | 12/2006 | Bromley et al. |
| 7,216,037 B2 | 5/2007 | Graulich et al. |
| 7,257,396 B2 | 8/2007 | Olsen et al. |
| 7,299,125 B2 | 11/2007 | Marks et al. |
| 7,313,467 B2 | 12/2007 | Breed et al. |
| 7,317,975 B2 | 1/2008 | Woolford et al. |
| 7,376,497 B2 | 5/2008 | Chen |
| 7,379,800 B2 | 5/2008 | Breed |
| 7,400,954 B2 | 7/2008 | Sumcad et al. |
| 7,408,453 B2 | 8/2008 | Breed |
| 7,421,321 B2 | 9/2008 | Breed et al. |
| 7,444,210 B2 | 10/2008 | Breed et al. |
| 7,457,693 B2 | 11/2008 | Olsen et al. |
| 7,467,034 B2 | 12/2008 | Breed et al. |
| 7,480,551 B1 | 1/2009 | Lowrey et al. |
| 7,486,181 B2 | 2/2009 | Olsen et al. |
| 7,527,288 B2 | 5/2009 | Breed |
| 7,555,370 B2 | 6/2009 | Breed et al. |
| 7,580,782 B2 | 8/2009 | Breed et al. |
| 7,603,894 B2 | 10/2009 | Breed |
| 7,630,802 B2 | 12/2009 | Breed |
| 7,650,210 B2 | 1/2010 | Breed |
| 7,657,354 B2 | 2/2010 | Breed et al. |
| 7,663,502 B2 | 2/2010 | Breed |
| 7,672,756 B2 | 3/2010 | Breed |
| 7,693,626 B2 | 4/2010 | Breed et al. |
| 7,715,961 B1 | 5/2010 | Kargupta |
| 7,734,390 B2 | 6/2010 | Chen |
| 7,760,080 B2 | 7/2010 | Breed et al. |
| 7,786,864 B1 | 8/2010 | Shostak et al. |
| 7,880,594 B2 | 2/2011 | Breed et al. |
| 7,889,096 B2 | 2/2011 | Breed |
| 8,036,788 B2 | 10/2011 | Breed |
| 2002/0049535 A1 | 4/2002 | Rigo et al. |
| 2002/0188392 A1 | 12/2002 | Breed et al. |
| 2003/0009270 A1 | 1/2003 | Breed |
| 2003/0055666 A1 | 3/2003 | Roddy et al. |
| 2003/0065771 A1 | 4/2003 | Cramer et al. |
| 2003/0093199 A1 | 5/2003 | Mavreas |
| 2003/0208309 A1 | 11/2003 | Triphathi |
| 2004/0024502 A1 | 2/2004 | Squires et al. |
| 2004/0039509 A1 | 2/2004 | Breed |
| 2004/0044452 A1 | 3/2004 | Bauer et al. |
| 2004/0078125 A1 | 4/2004 | Woodard et al. |
| 2004/0130442 A1 | 7/2004 | Breed et al. |
| 2004/0167689 A1 | 8/2004 | Bromley et al. |
| 2004/0215382 A1 | 10/2004 | Breed et al. |
| 2005/0038581 A1 | 2/2005 | Kapolka et al. |
| 2005/0125117 A1 | 6/2005 | Breed |
| 2005/0192727 A1 | 9/2005 | Shostak et al. |
| 2005/0222723 A1 | 10/2005 | Estes et al. |
| 2005/0273218 A1 | 12/2005 | Breed et al. |
| 2006/0025897 A1 | 2/2006 | Shostak et al. |
| 2006/0031042 A1 | 2/2006 | Ogura et al. |
| 2006/0055564 A1 | 3/2006 | Olsen et al. |
| 2006/0069473 A1 | 3/2006 | Sumcad et al. |
| 2006/0142934 A1 | 6/2006 | Kim |
| 2006/0180371 A1 | 8/2006 | Breed et al. |
| 2006/0212193 A1 | 9/2006 | Breed |
| 2006/0212194 A1 | 9/2006 | Breed |
| 2006/0243043 A1 | 11/2006 | Breed |
| 2006/0244581 A1 | 11/2006 | Breed et al. |
| 2006/0271246 A1 | 11/2006 | Bell et al. |
| 2006/0284839 A1 | 12/2006 | Breed et al. |
| 2007/0005202 A1 | 1/2007 | Breed |
| 2007/0057781 A1 | 3/2007 | Breed |
| 2007/0075919 A1 | 4/2007 | Breed |
| 2007/0096565 A1 | 5/2007 | Breed et al. |
| 2007/0103284 A1 | 5/2007 | Chew et al. |
| 2007/0124040 A1 | 5/2007 | Chen |
| 2007/0126561 A1 | 6/2007 | Breed |
| 2007/0139216 A1 | 6/2007 | Breed |
| 2007/0156312 A1 | 7/2007 | Breed et al. |
| 2007/0173991 A1 | 7/2007 | Tenzer et al. |
| 2007/0174004 A1 | 7/2007 | Tenzer et al. |
| 2007/0205881 A1 | 9/2007 | Breed |
| 2007/0239346 A1 | 10/2007 | Hawkins et al. |
| 2007/0271014 A1 | 11/2007 | Breed |
| 2007/0299587 A1 | 12/2007 | Breed et al. |
| 2008/0004764 A1 | 1/2008 | Chinnadurai et al. |
| 2008/0021604 A1 | 1/2008 | Bouvier et al. |
| 2008/0040005 A1 | 2/2008 | Breed |
| 2008/0042410 A1 | 2/2008 | Breed et al. |
| 2008/0046149 A1 | 2/2008 | Breed |
| 2008/0065290 A1 | 3/2008 | Breed et al. |
| 2008/0086240 A1 | 4/2008 | Breed |
| 2008/0114502 A1 | 5/2008 | Breed et al. |
| 2008/0129475 A1 | 6/2008 | Breed et al. |
| 2008/0140278 A1 | 6/2008 | Breed |
| 2008/0147265 A1 | 6/2008 | Breed |
| 2008/0147271 A1 | 6/2008 | Breed |

(56) References Cited

U.S. PATENT DOCUMENTS

| | | | |
|---|---|---|---|
| 2008/0154458 | A1 | 6/2008 | Brandstetter et al. |
| 2008/0161989 | A1* | 7/2008 | Breed .............................. 701/29 |
| 2008/0216567 | A1 | 9/2008 | Breed |
| 2008/0284575 | A1 | 11/2008 | Breed |
| 2009/0043441 | A1 | 2/2009 | Breed |
| 2009/0051566 | A1 | 2/2009 | Olsen et al. |
| 2009/0055045 | A1 | 2/2009 | Biswas et al. |
| 2009/0102638 | A1 | 4/2009 | Olsen et al. |
| 2009/0259358 | A1 | 10/2009 | Andreasen |
| 2010/0023203 | A1 | 1/2010 | Shibi |
| 2010/0138701 | A1 | 6/2010 | Costantino |
| 2010/0174446 | A1 | 7/2010 | Andreasen et al. |
| 2010/0207754 | A1 | 8/2010 | Shostak et al. |
| 2011/0118932 | A1* | 5/2011 | Singh et al. .................... 701/33 |
| 2012/0136743 | A1* | 5/2012 | McQuade et al. ........... 705/26.3 |
| 2012/0232743 | A1* | 9/2012 | Singh .......................... 701/29.9 |
| 2012/0239243 | A1* | 9/2012 | Medwin et al. .............. 701/31.6 |

OTHER PUBLICATIONS

International Searching Authority, International Search Report and Written Opinion for International Application No. PCT/US2012/048401, mailed Oct. 5, 2012, 11 pages, European Patent Office, The Netherlands.

Ciulla, Vincent T., "Auto Repair: Flash Codes," About.com, undated, 1 page, <http://autorepair.about.com/library/glossary/bldef-228.htm>, retrieved on Jun. 27, 2011.

Author Unknown, "On-Board Diagnostics," *Wikipedia*, undated, 10 pages, <http://en.wikipedia.org/wiki/On-board_diagnostics>, retrieved on Jun. 24, 2011.

Author Unknown, "SAE International," *Wikipedia*, undated, 5 pages, <http://en.wikipedia.org/wiki/SAE_International>, retrieved on Jun. 24, 2011.

Author Unknown, "SAE J 1857-2003 (SAE J1857-2003) Flywheel Dimensions for Truck and Bus Applications," *American National Standards Institute, Standards Store*, undated, 1 page, <http://webstore.ansi.org/RecordDetail.aspx?sku=SAE+J+1857-2003+(SAE+J1857-2003)>, retrieved on Jun. 24, 2011.

Author Unknown, "Telematics," *Wikipedia*, undated, 6 pages, <http://en.wikipedia.org/wiki/Telematics>, retrieved on Jun. 28, 2011.

Simma Software, "J1587 Protocol Stack Overview," Mar. 2, 2008 to Apr. 19, 2009, Internet Archive <web.archive.org/web/20090419231206/http://www.simmasoftware.com/j1587.html>, 1 page.

United States Patent & Trademark Office, Office Action for U.S. Appl. No. 12/419,818, Feb. 21, 2013, 11 pages, USA.

United States Patent & Trademark Office, Office Action for U.S. Appl. No. 12/419,818, Jun. 27, 2013, 11 pages, USA.

United States Patent and Trademark Office, Office Action for U.S. Appl. No. 12/419,818, Nov. 19, 2013, 16 pages, USA.

United States Patent and Trademark Office, Office Action for U.S. Appl. No. 12/419,818, Jun. 3, 2014, 10 pages, USA.

\* cited by examiner

FIG. 6

FIG. 7

SYSTEMS AND METHODS FOR MANAGING FAULT CODES

CROSS-REFERENCE TO RELATED APPLICATIONS

This application claims priority under 35 USC 119 to U.S. Provisional Application No. 61/511,660 filed Jul. 26, 2011, which is incorporated by reference herein in its entirety.

BACKGROUND

On-Board Diagnostics (OBD) on a vehicle refers to the vehicle's self-diagnostic and reporting capability. OBD systems provide information to individuals (such as automotive technicians) regarding the health of a vehicle's various sub-systems and components. Today, modern OBD systems provide real time data that typically includes standardized series of codes that may help an individual identify and remedy malfunctions within a vehicle (e.g., failures and/or possible failures). These codes include, for example, fault codes, flash codes, and diagnostic trouble codes (referred to collectively herein as "fault codes").

In many instances, vehicle manufacturers and manufacturers of various vehicle components may implement customized fault codes in addition to standardized series of codes, as well as provide customized diagnostics, recommendations, and instructions on how to address a particular code being triggered on a vehicle. For instance, the Ford Motor Company® may provide recommendations to address a particular fault code triggered by the antilock brake system on a Ford® vehicle and the General Motors Company® may provide different recommendations to address the same fault code triggered by the antilock brake system on a Chevrolet® vehicle. In addition, operators of such vehicles may develop customized diagnostics, recommendations, and instructions on how to address particular codes through experience on addressing such codes triggered on one or more vehicles the operators own and operate. Although the fault codes may provide some information regarding a problem with a particular component or system, the information is typically binary (i.e. good or bad). The codes do not provide any indication of the severity of the problem, which can result in unnecessary or premature replacement or repair of vehicle components. Thus, a need exists for providing systems and methods for managing such codes, mechanisms for triggering responses to such codes, and mechanisms for addressing such codes.

BRIEF SUMMARY OF VARIOUS EMBODIMENTS OF THE INVENTION

Various embodiments of the present invention provide systems and methods for managing fault codes associated with a vehicle. For instance, in particular embodiments, the systems and methods involve receiving fault code information retrieved from the vehicle. In these particular embodiments, the fault code information includes one or more fault codes generated during a particular time period the vehicle was in operation and the systems and methods involve analyzing the fault code information based on one or more parameters associated with the fault codes from the fault code information. Such an analysis is performed in these embodiments in order to identify fault codes signaling failure or potential failure of one or more components or sub-systems of the vehicle.

In addition, in particular embodiments, the systems and methods may involve setting a state for each of the identified fault codes indicating a level of action to address the identified fault code. For instance, the state may be set to one of a caution state indicating the one or more components or sub-systems of the vehicle should be monitored, a critical state indicating the one or more components or sub-systems of the vehicle should be repaired, or an environmental state indicating the failure or potential failure of the one or more components or sub-systems of the vehicle affects one or more environmental conditions. Further, in various embodiments, the systems and methods may involve sending one or more notifications to one or more parties for each of the identified fault codes that lists the state set for each of the identified fault codes and/or may involve initiating a work order for repair of at least one of the one or more components or sub-systems of the vehicle.

Further, in various embodiments, the systems and methods may involve providing an interface. In particular embodiments, the interface may provide access to one or more procedures for diagnosing and/or performing maintenance on one or more components or sub-systems associated with each of the identified fault codes. These diagnostic and/or maintenance procedures may be dependent on manufacturers of the components or sub-systems of the vehicle. In addition, the interface may display comments provided by one or more individuals on results of performing one or more of the diagnostic and/or maintenance procedures and may provide a map displaying the GPS coordinates of the vehicle.

In addition, in various embodiments, a particular fault code may be associated with at least one set of parameters. In particular embodiments, the set of parameters may include an upper limit and a lower limit providing a range of a number of times the fault code is generated during the particular time period the vehicle was in operation. In these particular embodiments, the systems and methods may involve setting the state for the particular fault code in response to the fault code information showing the particular fault code was generated within the range during the particular time period the vehicle was in operation.

Finally, in various embodiments, a particular fault code may be associated with a set of parameters that includes a threshold value providing a number of times the particular fault code is generated during a particular time period or over a particular set of distance the vehicle was in operation and a consecutive value providing a number of consecutive time periods or consecutive sets of distance. In these particular embodiments, the systems and methods may involve setting the state for the particular fault code in response to the number of times the particular fault code is generated during the particular time period or over the particular set of distance is at least the threshold value for a number of consecutive time periods or consecutive sets of distance equal to the consecutive value.

BRIEF DESCRIPTION OF THE SEVERAL VIEWS OF THE DRAWING(S)

Figure 2:
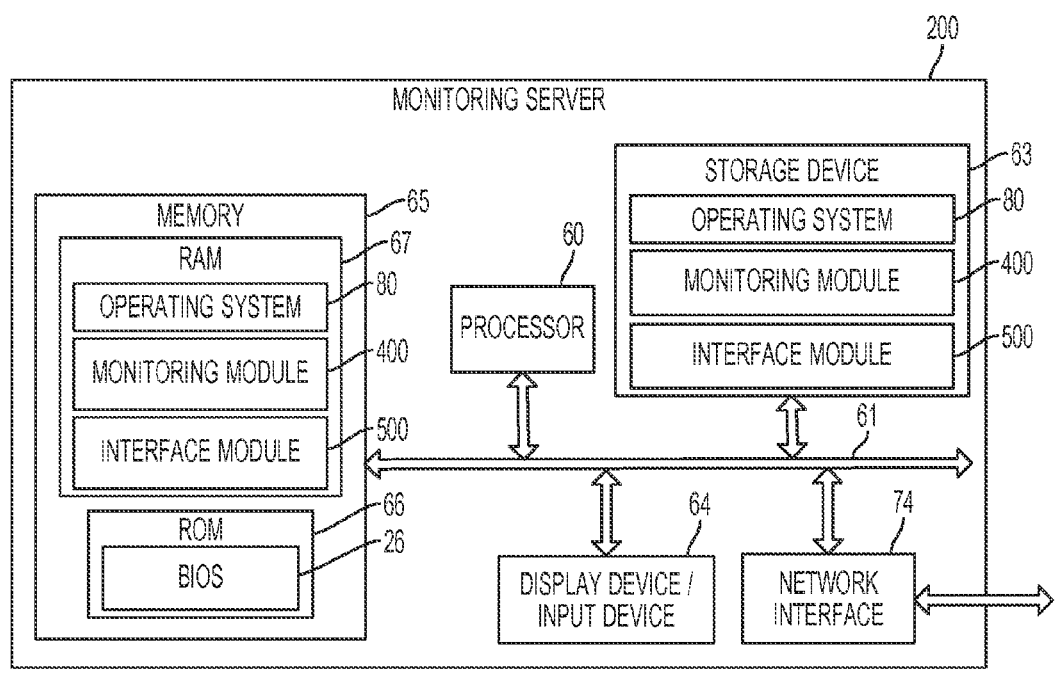
Figure 3:
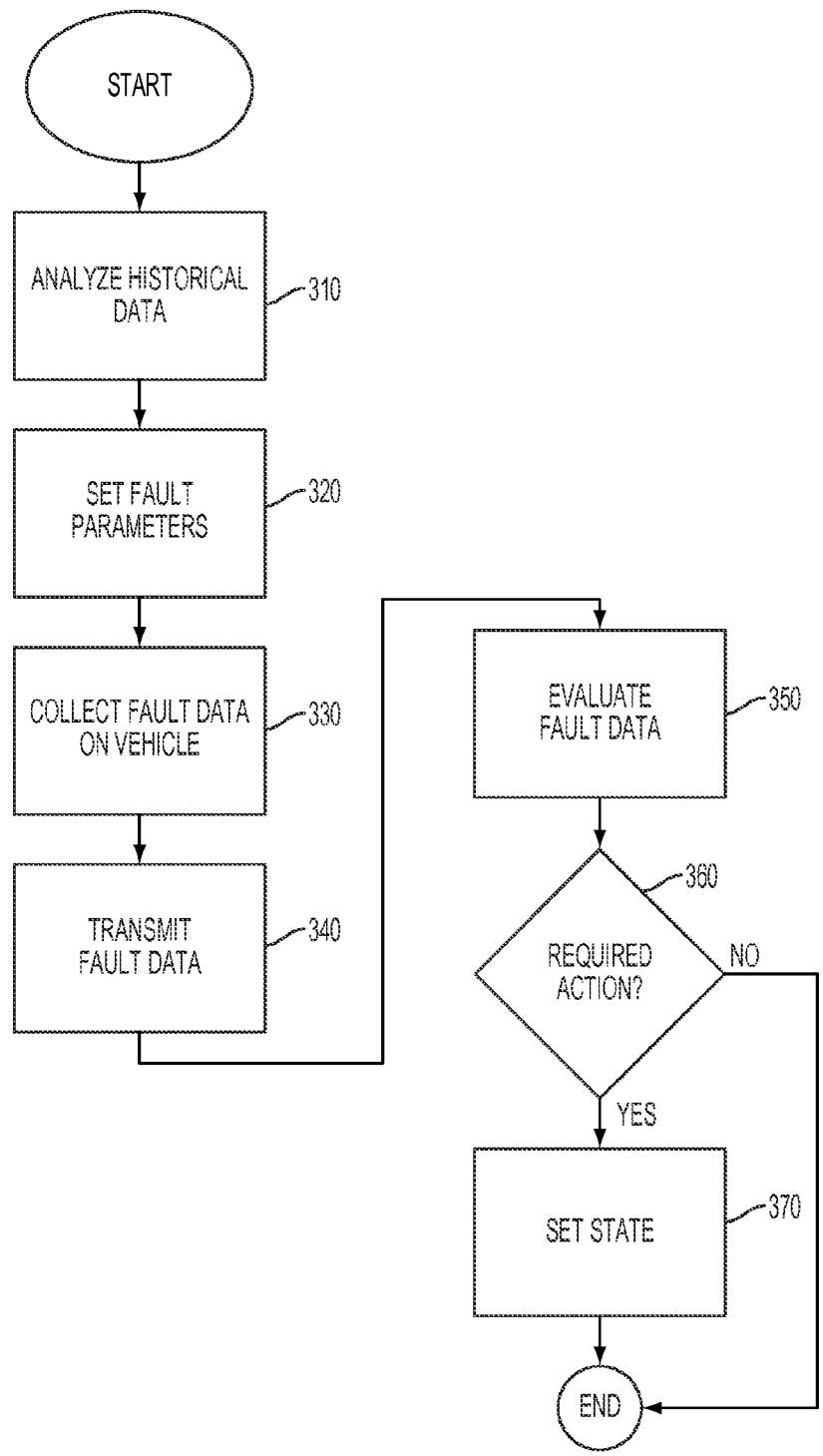
Figure 4:
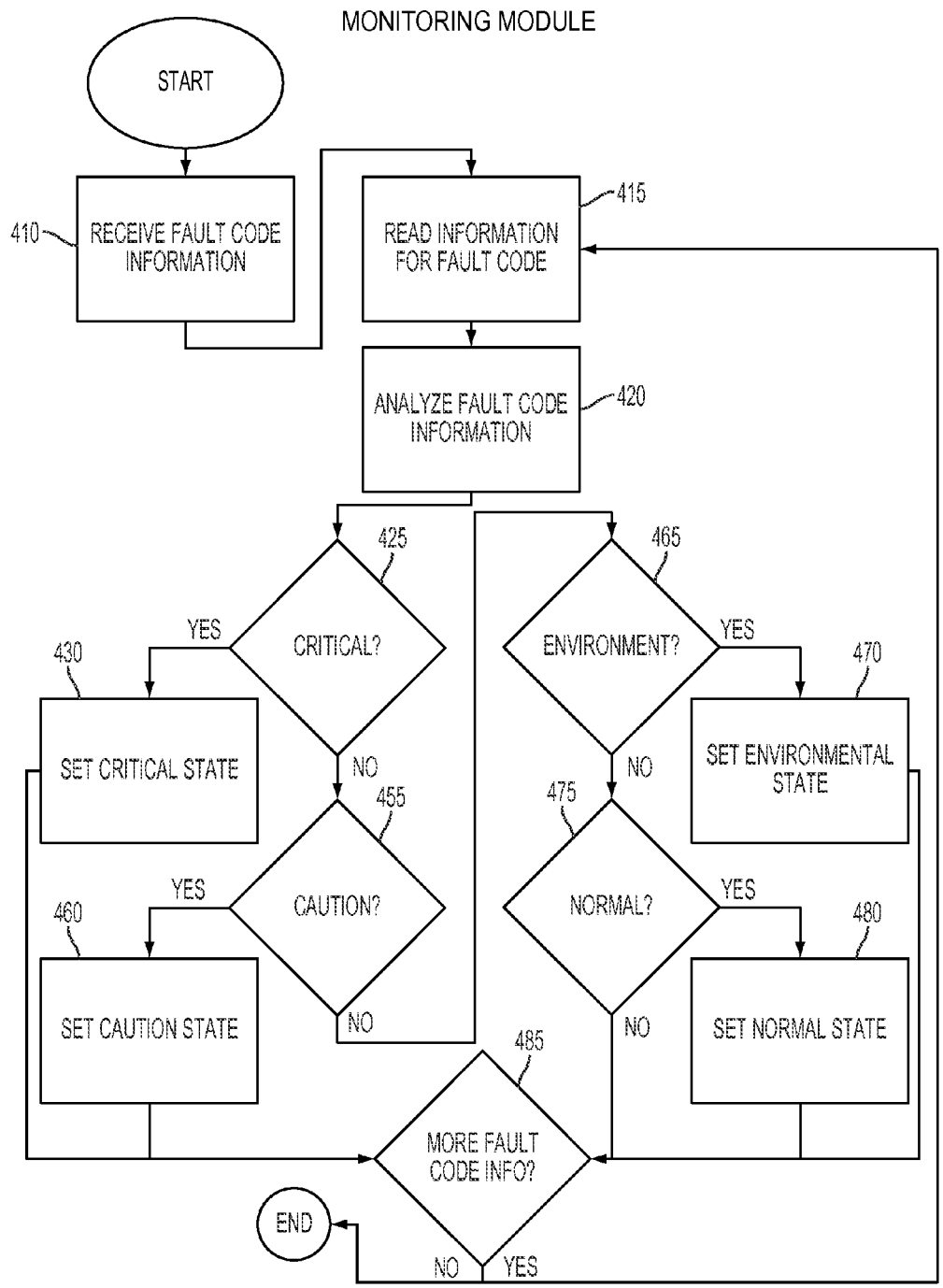
Figure 5:
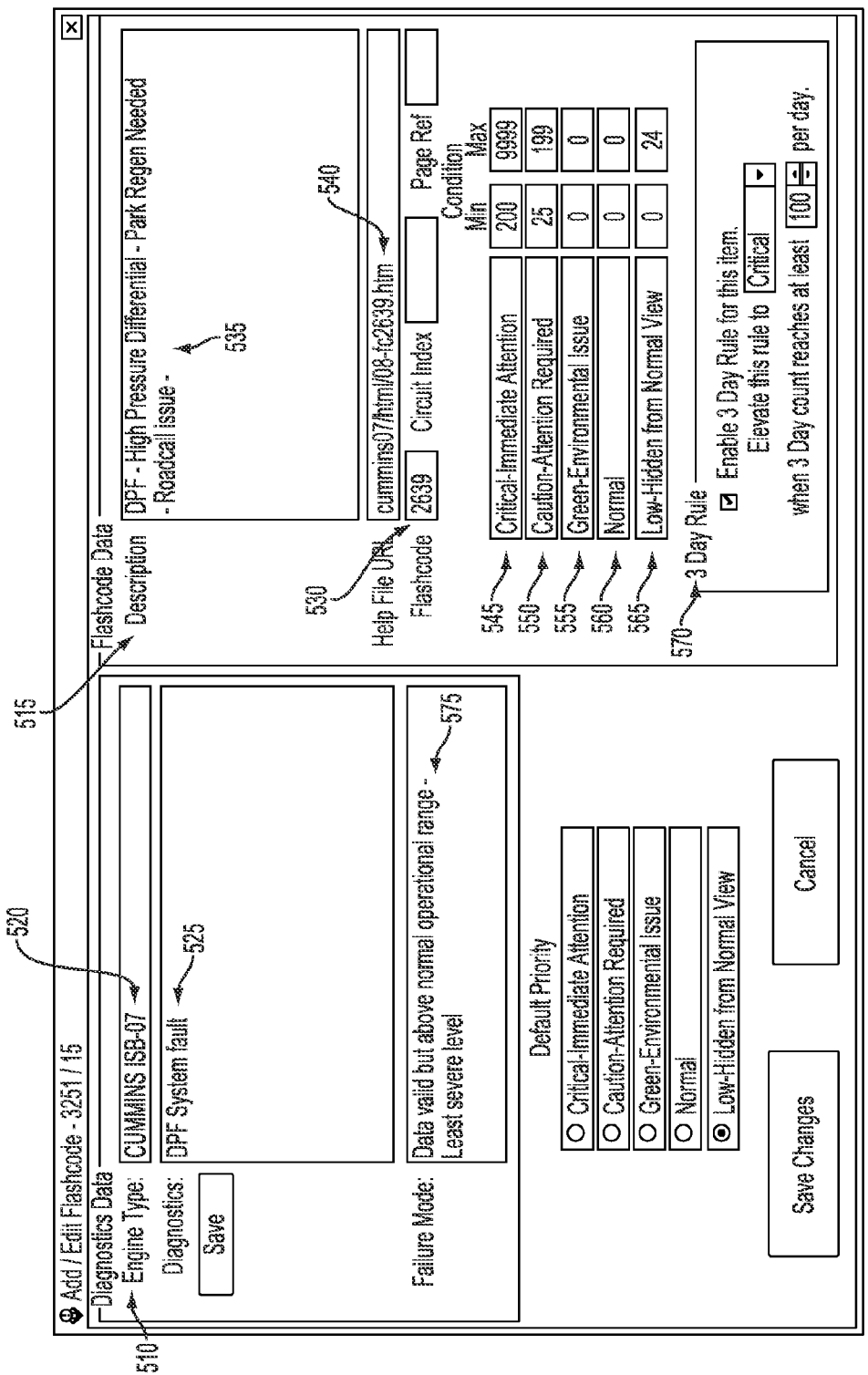
Figure 8:
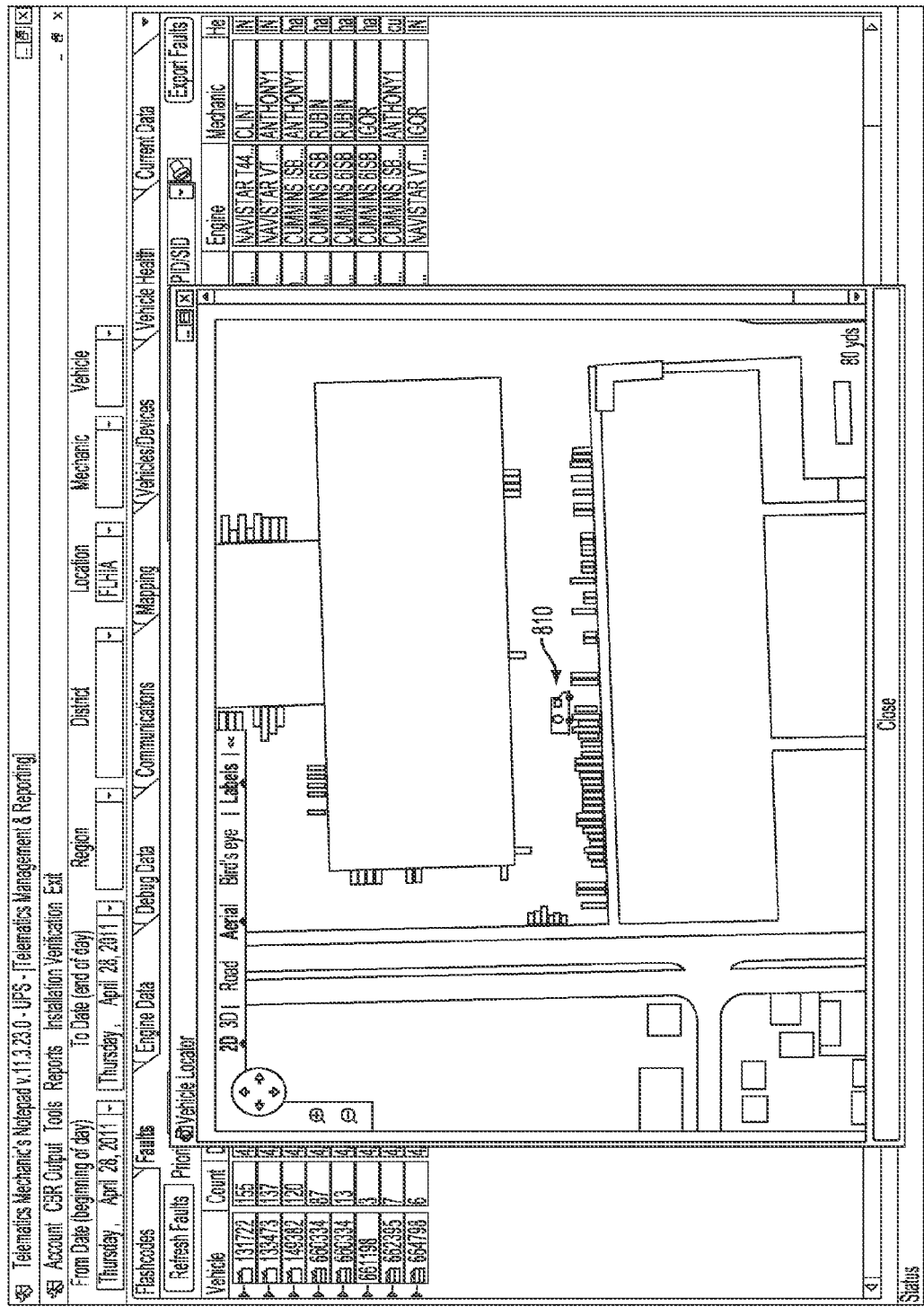

Having thus described the invention in general terms, reference will now be made to the accompanying drawings, which are not necessarily drawn to scale, and wherein:

FIG. 1 provides a schematic diagram of a system architecture for practicing various aspects of embodiments of the present invention;

FIG. 2 provides a schematic diagram of a monitoring server according to one embodiment of the present invention;

FIG. 3 provides a flow diagram of a monitoring process according to one embodiment of the present invention;

FIG. 4 provides a flow diagram of steps executed by a monitoring module according to one embodiment of the present invention;

FIG. 5 provides an interface screen according to one embodiment of the present invention;

Figure 6:
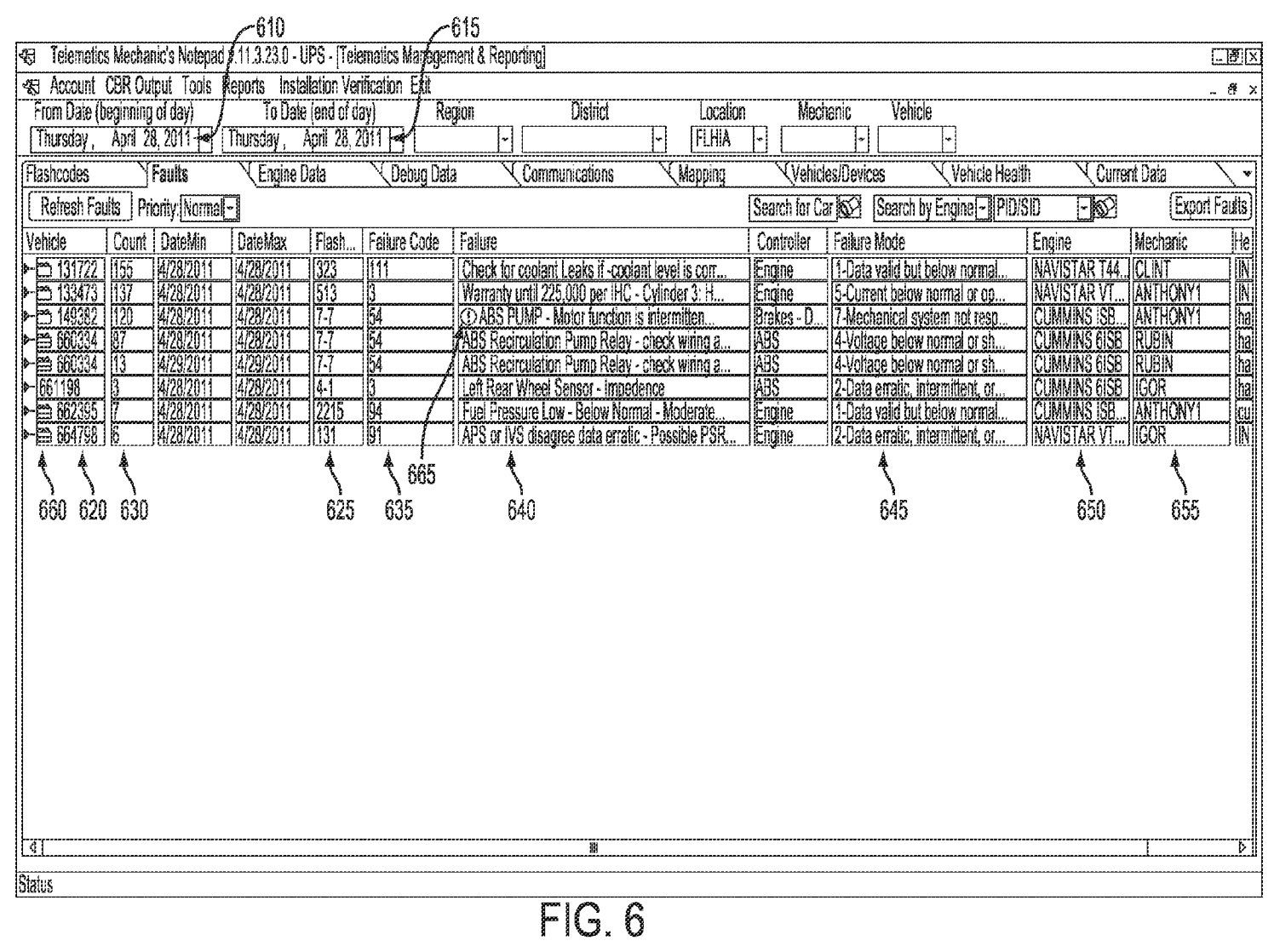

FIG. 6 provides another interface screen according to one embodiment of the present invention;

Figure 7:
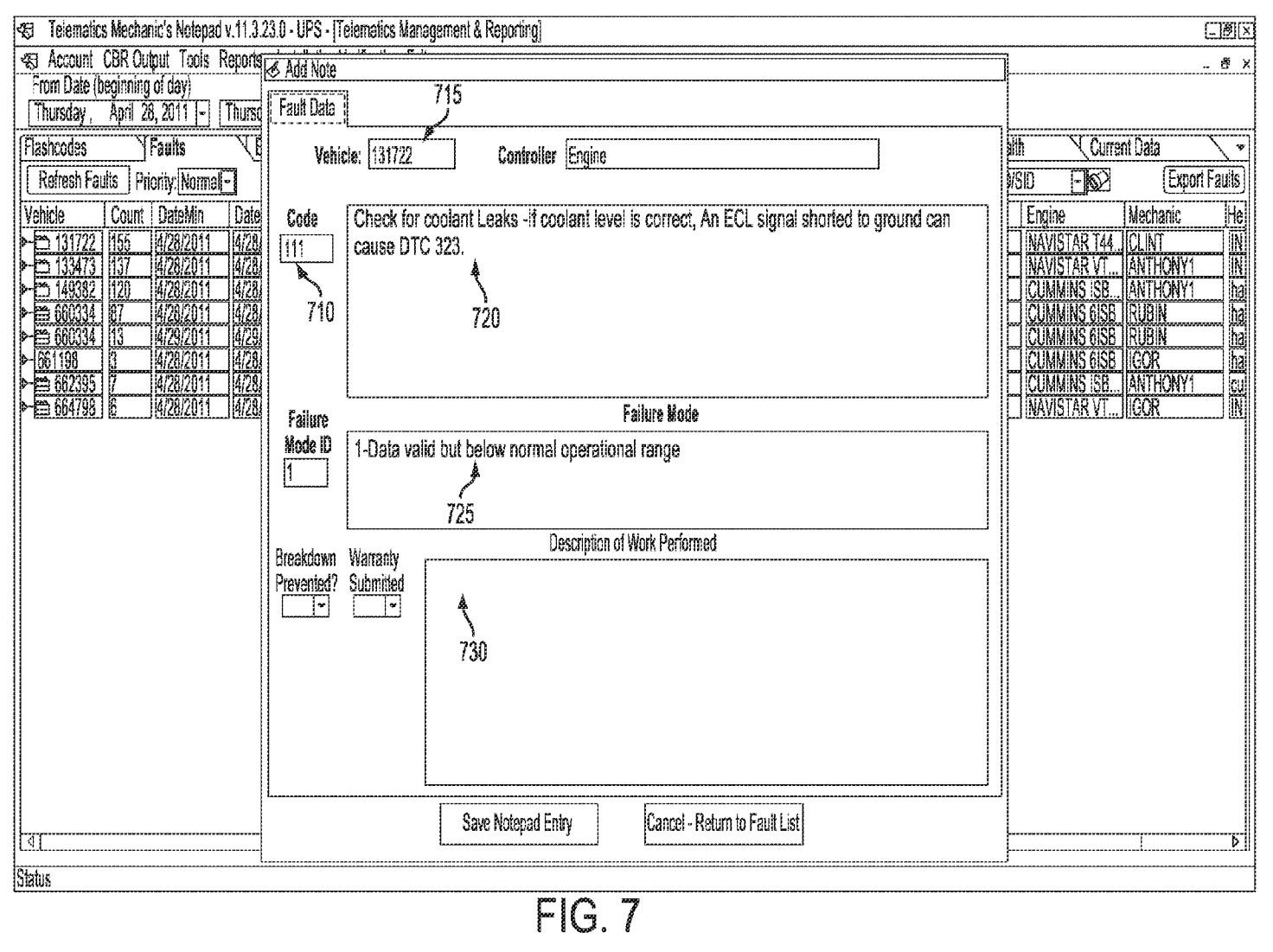

FIG. 7 provides another interface screen according to one embodiment of the present invention; and FIG. 8 provides another interface screen according to one embodiment of the present invention.

DETAILED DESCRIPTION OF VARIOUS EMBODIMENTS OF THE INVENTION

Various embodiments of the present invention now will be described more fully hereinafter with reference to the accompanying drawings, in which some, but not all embodiments of the inventions are shown. Indeed, these inventions may be embodied in many different forms and should not be construed as limited to the embodiments set forth herein. Rather, these embodiments are provided so that this disclosure will satisfy applicable legal requirements. The term "or" is used herein in both the alternative and conjunctive sense, unless otherwise indicated. Like numbers refer to like elements throughout.

I. METHODS, APPARATUS, SYSTEMS, AND COMPUTER PROGRAM PRODUCTS

As will be appreciated from the description herein, the embodiments of the present invention may be implemented in various ways, including as methods, apparatuses, systems, or computer program products. Accordingly, the embodiments may take the form of an entirely hardware embodiment or an embodiment in which a processor is programmed to perform certain steps. Furthermore, the various implementations may take the form of a computer program product on a computer-readable storage medium having computer-readable program instructions embodied in the storage medium. Any suitable computer-readable storage medium may be utilized including hard disks, CD-ROMs, optical storage devices, or magnetic storage devices.

Particular embodiments are described below with reference to block diagrams and flowchart illustrations of methods, apparatus, systems, and computer program products. It should be understood that each block of the block diagrams and flowchart illustrations, respectively, may be implemented in part by computer program instructions (e.g., as logical steps or operations executing on a processor in a computing system). These computer program instructions may be loaded onto a computer, such as a special purpose computer or other programmable data processing apparatus to produce a specifically-configured machine, such that the instructions which execute on the computer or other programmable data processing apparatus implement the functions specified in the flowchart block or blocks.

These computer program instructions may also be stored in a computer-readable memory that can direct a computer or other programmable data processing apparatus to function in a particular manner such that the instructions stored in the computer-readable memory produce an article of manufacture including computer-readable instructions for implementing the functionality specified in the flowchart block or blocks. The computer program instructions may also be loaded onto a computer or other programmable data processing apparatus to cause a series of operational steps to be performed on the computer or other programmable apparatus to produce a computer-implemented process such that the instructions that execute on the computer or other programmable apparatus provide operations for implementing the functions specified in the flowchart block or blocks.

Accordingly, blocks of the block diagrams and flowchart illustrations support various combinations for performing the specified functions, combinations of operations for performing the specified functions, and program instructions for performing the specified functions. It should also be understood that each block of the block diagrams and flowchart illustrations, as well as combinations of blocks in the block diagrams and flowchart illustrations, can be implemented by special purpose hardware-based computer systems that perform the specified functions or operations, or combinations of special purpose hardware and computer instructions.

II. SYSTEM ARCHITECTURE

FIG. 1 provides a schematic diagram of a system architecture for practicing various aspects of embodiments of the present invention. The system is made up of one or more vehicles 110 traveling over roadways from day-to-day. For instance, in one embodiment, the vehicles 110 are part of a fleet, such as a common carrier delivery fleet that may include local delivery trucks, tractor trailers, delivery vans, and other vehicles used by the common carrier to transport packages within the common carrier's delivery network. Other vehicle fleets may include buses, taxis, refuse trucks, meter reader vehicles, and the like. In particular embodiments, one or more of the vehicles 110 include an engine control module (ECM) 130 configured to control the vehicle's engine 120. The ECM is a type of electronic control unit that controls various engine dynamics by determining ignition timing, fuel amounts, and other parameters for an engine 120. In various embodiments, the ECM 130 may be configured to interpret signals received from sensor devices monitoring the engine 120 by reading values from multidimensional performance maps (e.g., look up tables) and using input values (e.g., engine speed) calculated from the received signals.

In particular embodiments, the ECM 130 includes a microprocessor that processes inputs from engine sensors in real time. In these particular embodiments, the ECU 130 may contain hardware and software. The hardware may include electronic components on a printed circuit board (PCB), ceramic substrate, or a thin laminate substrate. The main component on the circuit board may be a microcontroller chip (CPU). In addition, the software may be stored in the microcontroller or other chips on the PCB, in erasable programmable read only memory (EPROMs), or in flash memory so that the CPU can be re-programmed by uploading updated code or replacing chips. In many instances, such a configuration is referred to as an electronic Engine Management System (EMS).

In particular embodiments, the EMS may receive inputs from other sources and may control other parts of the engine. For instance, the EMS may electronically control and manage a variable valve timing system and turbocharger wastegates. In addition, the EMS may also communicate with transmission control units or directly interface with electronically-controlled automatic transmissions, traction control systems, and the like. In many instances, the Controller Area Network or CAN bus automotive network is often used to achieve communication between these devices. Further, in particular instances, the ECM triggers diagnostic information known as fault codes, flash codes, or trouble codes, as they are often referenced, to identify and remedy malfunctions within a vehicle (e.g., to identify and remedy one or more failures and/or possible failures of one or more components and/or sub-systems of the vehicle).

For example, in particular vehicles 110, the ECM 130 receives signals such as crankshaft position, camshaft position, engine speed, and engine coolant temperature and, in response, sends ON/OFF pulse duty signals to the intake valve timing control solenoid valve. This can be done, for example, depending on driving status to make it possible to control the shut/open timing of the intake valve in order to increase engine torque in low/mid speed range and output in high-speed range. In these vehicles 110, the intake valve timing control solenoid valve changes the oil amount and direction of flow through an intake valve timing control unit or stops oil flow. Longer pulse width advances valve angle and shorter pulse width retards valve angle. Thus, when ON and OFF pulse widths become equal, the solenoid valve stops oil pressure flow to fix the intake valve angle at the control position. However, when a gap exists between a target angle and phase-control angle degree, the solenoid valve stops working. As a result, the ECM 130 triggers a P0021 fault code to signal the valve has stopped working. This fault code may then be read by an individual (e.g., automotive technician) to diagnose the valve failure so that the valve may be repaired or replaced.

In particular embodiments, the vehicle 110 also includes a telematics system 140 that receives information such as fault codes from the ECM 130. In general, telematics systems are configured to collect information from various control systems and sensors located on a vehicle and transmit the information through a communications network (e.g., a cellular, WAN, or other wireless network). Thus, in particular embodiments, the telematics system 140 on the vehicle 110 receives information on various fault codes triggered from the ECM 130 and transmits the information over a communication network 150 (e.g., a mobile cellular network) to a central location. For instance, in embodiments in which the communication network 150 comprises a mobile cellular network, the telematics system 140 may transmit the information over the network 150 to a base station 160 within the network 150 and the cellular carrier may be in electronic communication with a central monitoring system 180 over one or more wireless or wired networks 170 (e.g, a wired or wireless Personal Area Network ("PAN"), Local Area Network ("LAN"), Metropolitan Area Network ("MAN"), Wide Area Network ("WAN"), the Internet, or the like).

Thus, returning to the example involving vehicles 110 that are part of a common carrier delivery system, the telematics systems 140 of the one or more vehicles 110 in the common carrier's fleet transmit fault code information over the network 150 to the central monitoring system 180 located within the common carrier's infrastructure. In various embodiments, the vehicles 110 may transmit the information based on some predetermined time period such as once a day or once every three hours. In other embodiments, the vehicles 110 may transmit the information based on some triggering event, such as the vehicle's return to a service center after completing a delivery route, after traveling a particular distance, or the triggering of a particular fault code.

Furthermore, according to various embodiments, the monitoring system 180 may be in electronic communication with one or more types of storage media 190. For instance, in particular embodiments, the storage media 190 may be one or more types of media such as hard disks, magnetic tapes, or flash memory. In addition, in particular embodiments, the monitoring system 180 may include a database management system and the storage media 190 may include one or more databases and one or more database instances. As used herein, the term "database" refers to a structured collection of records or data that is stored in a computer system, such as via a relational database, hierarchical database, or network database. As is discussed in further detail below, in particular embodiments, the storage media 190 may be used to store information received from the vehicles 110 as well as parameters used to evaluate the information received from the vehicles 110.

Finally, while FIG. 1 illustrates the architecture according to one embodiment of the invention, it should be understood that the various components of the architecture, as described above, may be configured differently in other embodiments. Therefore, the various aspects of the claimed invention are not limited to this particular architecture.

III. MONITORING SERVER

In various embodiments, the monitoring system 180 may include one or more computing devices (e.g., one or more servers). FIG. 2 provides a schematic of a monitoring server 200 according to one embodiment of the present invention. As used herein, the term "server" is used generically to refer to any computer, computing device, desktop, notebook or laptop, distributed system, server, gateway, switch, or other processing device adapted to perform the functions described herein.

As shown in the illustrated embodiment of FIG. 2, the monitoring server 200 includes a processor 60 that communicates with other elements within the monitoring server 200 via a system interface or bus 61. The processor 60 may be embodied in a number of different ways. For example, the processor 60 may be embodied as various processing means such as a processing element, a microprocessor, a coprocessor, a controller, or various other processing devices including integrated circuits such as, for example, an application specific integrated circuit ("ASIC"), a field programmable gate array ("FPGA"), a hardware accelerator, or the like. In an exemplary embodiment, the processor 60 may be configured to execute instructions stored in the device memory or otherwise accessible to the processor 60. As such, whether configured by hardware or software methods, or by a combination thereof, the processor 60 may represent an entity capable of performing operations according to embodiments of the present invention while configured accordingly. A display device/input device 64 for receiving and displaying data is also included in the monitoring server 200. This display device/input device 64 may be, for example, a keyboard or pointing device that is used in combination with a monitor. The monitoring server 200 further includes memory 65, which may include both read only memory ("ROM") 66 and random access memory ("RAM") 67. The application server's ROM 66 may be used to store a basic input/output system ("BIOS") 26 containing the basic routines that help to transfer information to the different elements within the monitoring server 200.

In addition, in one embodiment, the monitoring server 200 includes at least one storage device 63, such as a hard disk drive, a CD drive, and/or an optical disk drive for storing information on various computer-readable media. The storage device(s) 63 and its associated computer-readable media may provide nonvolatile storage. The computer-readable media described above could be replaced by any other type of computer-readable media, such as embedded or removable multimedia memory cards ("MMCs"), secure digital ("SD")

memory cards, Memory Sticks, electrically erasable programmable read-only memory ("EEPROM"), flash memory, hard disk, or the like. Additionally, each of these storage devices 63 may be connected to the system bus 61 by an appropriate interface.

Furthermore, a number of program modules (e.g., set of computer program instructions) may be stored by the various storage devices 63 and/or within RAM 67. Such program modules may include an operating system 80, a monitoring module 400, and an interface module 500. These modules 400, 500, may control certain aspects of the operation of the monitoring server 200 with the assistance of the processor 60 and operating system 80, although their functionality need not be modularized.

Also located within the monitoring server 200, in one embodiment, is a network interface 74 for interfacing with various computing entities. This communication may be via the same or different wired or wireless networks (or a combination of wired and wireless networks), as discussed above. For instance, the communication may be executed using a wired data transmission protocol, such as fiber distributed data interface ("FDDI"), digital subscriber line ("DSL"), Ethernet, asynchronous transfer mode ("ATM"), frame relay, data over cable service interface specification ("DOCSIS"), or any other wired transmission protocol. Similarly, the monitoring server 200 may be configured to communicate via wireless external communication networks using any of a variety of protocols, such as 802.11, general packet radio service ("GPRS"), wideband code division multiple access ("W-CDMA"), or any other wireless protocol.

It will be appreciated that one or more of the monitoring server's 200 components may be located remotely from other monitoring server 200 components (e.g., distributed across multiple monitoring servers 200). Furthermore, one or more of the components may be combined and additional components performing functions described herein may be included in the monitoring server 200.

IV. GENERAL OVERVIEW OF MONITORING PROCESS

FIG. 3 provides a general overview of a fleet monitoring processing according to an embodiment of the invention. In this particular instance, the process entails the recording and analyzing of fault codes triggered during a particular time period while a vehicle 110 is in operation.

In the illustrated embodiment of FIG. 3, the monitoring process is adapted for implementation by a common carrier in order to monitor its delivery fleet. The first step of the monitoring process involves establishing parameters to evaluate the various fault codes that may be received from a particular vehicle 110. Accordingly, in Step 310, the monitoring process begins with analyzing historical data collected on fault codes received from different vehicles 110 within the common carrier's fleet and on maintenance performed on the different vehicles 110 as a result of the fault codes being triggered. The purpose of conducting this particular step in various embodiments is to establish relationships between fault codes received for particular vehicles 110 and maintenance required on these particular vehicles 110 as a result of the fault codes being triggered. In addition, this particular step may involve reviewing procedures provided by different vehicle and component manufacturers for addressing various fault codes. For example, a particular fault code may indicate a problem with the flywheel configuration used with pull type single and twin plate truck clutches. However, depending on the manufacturer of the vehicle 110 and/or the particular clutch on the vehicle 110, the procedure for addressing a malfunction of the flywheel may be different. Thus, in particular embodiments, the analysis step may also involve considering these different procedures for different vehicle and component manufacturers.

Once the analysis is completed, the monitoring process continues to Step 320 where parameters are set for various fault codes. In particular embodiments, parameters are set for each fault code that may be received from a particular vehicle 110 in order to evaluate the fault code and to make a determination on how to address a triggering of the fault code. As will be appreciated from the description herein, these parameters may be defined in different ways according to various embodiments.

For instance, in one embodiment, the parameters may be defined so that if a particular fault code received for a vehicle 110 falls within a certain set of parameters, a particular action is taken with respect to the fault code. For example, Table 1 illustrates parameters established for a particular fault code associated with a particular component on a vehicle 110 (e.g., fault code 111).

TABLE 1

| State | Action | Condition | |
|---|---|---|---|
| | | Minimum | Maximum |
| Critical | Take Immediate Action | 200 | 9999 |
| Caution | Monitor | 25 | 199 |
| Normal | No Action | 0 | 24 |

Thus, based on these particular parameters illustrated in Table 1, if the particular fault code 111 is triggered less than 25 times, the state for the fault code 111 remains normal and no action is taken. However, if the fault code 111 is triggered between twenty-five (25) and one-hundred and ninety-nine (199) times during a particular time period the vehicle 110 was in operation (e.g., twenty-four hours), the state for the fault code 111 is changed to "Caution" and the action taken is to monitor the component associated with fault code 111. If fault code 111 is triggered between two-hundred (200) and nine-thousand nine-hundred and ninety-nine times during the predetermined time period, the state for the fault code is changed to "Critical" and the associated action is to take immediate action to address the triggered fault code. Such immediate action may involve, for example, scheduling the vehicle 110 for repair or replacing the component associated with the particular fault code. As should be understood, the states, actions, and conditions (e.g., minimums and maximums) are for illustration purposes only and are not meant to be limiting. Indeed, any states, actions, and associated conditions may be established for the various fault codes as desired.

Furthermore, the parameters for a particular fault code may include parameters that apply to different manufacturers. For instance, returning to the example of the parameters set for fault code 111 in Table 1, the parameters may be set differently for Manufacturer A and for Manufacturer B of the component as shown in Table 2.

TABLE 2

| State | Action | Condition | |
|---|---|---|---|
| | | Minimum | Maximum |
| Manufacturer A | | | |
| Critical | Take Immediate Action | 200 | 9999 |
| Caution | Monitor | 25 | 199 |
| Normal | No Action | 0 | 24 |

TABLE 2-continued

| | | Condition | |
|---|---|---|---|
| State | Action | Minimum | Maximum |
| Manufacturer B | | | |
| Critical | Take Immediate Action | 150 | 9999 |
| Caution | Monitor | 20 | 149 |
| Normal | No Action | 0 | 19 |

As noted above, such differences between manufacturers may be the result of the analysis conducted on the historical information for various vehicles 110 in the common carrier's fleet that include the component from both Manufacturer A and Manufacturer B, as well as the different procedures and information provided by the manufacturers on addressing a malfunction of the component.

Once the parameters for the various fault codes have been established, the monitoring process continues at Step 330 where fault data is collected from one or more vehicles 110. Thus, for a particular delivery vehicle 110, fault data is collected by the vehicle's telematics system 140 during the vehicle's travel along its delivery route. Next, in Step 340, the fault data is transmitted over the communication network 150 (e.g., a wireless cellular network) and is received at a central location for the common carrier. The fault data may be transmitted at different times based on different criteria according to various embodiments. For instance, the fault data may be transmitted at a particular time period (e.g., once every twenty-four hours or once every eight hours) or the fault data may be transmitted based on a triggering event (e.g., the detection of the vehicle returning to a service center after completing its delivery route, the detection of traveling a certain distance, or the detection of a particular fault code or type of fault code).

In addition, it should be noted that the fault data does not necessarily need to be transmitted from the vehicle over the network 150. For instance, in various embodiments, the fault data may be retrieved from the telematics system 140 and/or the ECM 130 directly by downloading or otherwise transferring the data from the telematics system 140 and/or the ECM 130 to a portable storage device, such as a flash drive, memory stick, portable hard drive or the like. However, in instances in which it is desirable to evaluate the fault data in near real time, the transmission of the fault data over the communication network 150 may be preferred.

Next, in Step 350, the process continues with evaluating the fault data using the appropriate parameters to determine whether an action should be taken with respect to fault codes triggered during the data collection period. For instance, assume the fault data received from a particular vehicle 110 shows fault code 111 was triggered one-hundred and seventy-two (172) times during the data collection period and the component associated with the fault code was manufactured by Manufacturer B. Next, at Step 360, the process determines whether the one-hundred and seventy-two counts indicates a failure or possible failure of the particular component and whether some type of action should be taken in light of the count. First, a determination is made as to whether the component was manufactured by Manufacturer A or Manufacturer B. To make such a determination, in particular embodiments, maintenance records may be reviewed to determine the current component installed on the vehicle 110. Once the manufacturer of the component has been established, the fault code count is compared to the appropriate set of parameters, which for this example is set forth in Table 2 above. Thus, in this instance, since the component was manufactured by Manufacturer B, a determination is made that the component should be repaired or replaced. As a result, a state is set for fault code 111-indicating the level of action to be taken to address the fault code is to repair or replace the component associated with fault code 111, shown as Step 370.

In particular embodiments, the required action based on the evaluation may be communicated to one or more appropriate parties. For instance, if the component is in need of repair or replacement, a notification may be sent to maintenance personnel to alert them of the needed repair or replacement of the component on the vehicle 110. In addition, other parties may be notified (e.g., operations to alert them that the vehicle may not be available for a particular time period, an inventory system to order a replacement part if needed).

Thus, the above-mentioned process allows for the management of fault codes received from one or more vehicles 110 of the common carrier's fleet. In addition, such a process allows for the management of how to handle detection of such fault codes from the vehicles 110 based not only on the number of times the fault codes are triggered over a particular time period but also from the perspective of different manufacturers of the vehicles 110, sub-systems, and/or components associated with triggered fault codes.

V. EXEMPLARY SYSTEM OPERATION

Reference will now be made to FIGS. 4-8 which illustrate operations and processes as produced by various embodiments of the invention. For instance, FIG. 4 provides a flow diagram of steps executed by the monitoring module 400. FIGS. 5-8 provide interface screen shots used by various individuals with respect to different aspects of the monitoring system. The monitoring module 400 and screens are described in greater detail below.

a. Monitoring Module

As previously described, in various embodiments, the monitoring system 180 (e.g., the monitoring server 200) includes a monitoring module 400 configured to evaluate the fault code information received from a particular vehicle 110. FIG. 4 illustrates a flow diagram of the monitoring module 400 according to a particular embodiment. This flow diagram may correspond to the steps carried out by the processor 60 in the monitoring server 200 shown in FIG. 2 as it executes the monitoring module 400 in the server's RAM memory 67 according to various embodiments.

Thus, starting with Step 410, the monitoring module 400 receives the fault code information for a particular vehicle 110. As previously explained, in various embodiments, such information is gathered by a vehicle's telematics system 140 during the operation of the vehicle 110 and the information is transmitted to the monitoring system 180. In addition, in particular embodiments, the fault code information may include additional information to identify the particular vehicle and the time period in which the fault code information was collected. Thus, the monitoring module 400 is able to identify the particular vehicle 100 and the particular time period associated with the fault code information. Not only is such information helpful in notifying appropriate parties of vehicles 110 requiring attention, but such information may also be helpful in instances in which the monitoring module 400 retrieves historical information on the particular vehicle 110 such as fault code information for previous time periods and/or information on the model and make of the vehicle 110 and the components installed on the vehicle 110.

Next, in Step 415, the monitoring module 400 reads information from the fault code information for a particular fault code triggered during the recording period. As previously mentioned, in particular embodiments, parameters are set for different fault codes to be used to conduct an evaluation on information received for a particular fault code from the vehicle 110. Thus, in these particular embodiments, the monitoring module 400 may retrieve the parameters from the one or more storage media 190 so that the parameters may be used for the evaluation. The storage media 190 in particular embodiments may include one or more databases for storing the parameters. Thus, in these particular embodiments, the monitoring module 400 queries the parameters from the databases based on information such as, for instance, the make and model of the vehicle 110, the fault code triggered during operation of the vehicle 110, and/or the part number of one or more components and/or sub-systems associated with the fault code.

Once the parameters have been retrieved, the monitoring module 400 moves to Step 420, where it performs an analysis of the fault code information for the particular fault code based on the parameters. For instance, as previously mentioned, the parameters may set boundaries for triggering particular required actions to be taken with regard to the particular fault code being triggered during operation of the vehicle 110. For example, the parameters may include an upper limit and a lower limit for the number of times a particular fault code is triggered during the time period in which the fault code information was recorded. In this particular example, the monitoring module 400 determines whether the number of times the particular fault code was triggered during the recording period is between the upper and lower limits. If so, the monitoring module 400 sets a state indicating the appropriate/required actions to be taken with respect to the triggered fault code.

As one of ordinary skill in the art can envision in light of this disclosure, the parameters for a particular fault code may be defined in multiple ways according to various embodiments. For instance, in one embodiment, the parameters may include sets of parameters for a "Critical" state which may indicate immediate attention is required, for a "Caution" state which may indicate monitoring is required, for an "Environmental" state which may indicate a failure or potential failure of one or more components and/or sub-systems associated with the fault code may involve environmental issues, for a "Normal" state, and for a "Low Occurrence" state.

In particular embodiments, a set of parameters for a "Critical" state may include a minimum set point (e.g., lower limit) and/or a maximum set point (e.g., upper limit). For instance, if the monitoring module 400 determines the number of times the fault code was triggered during the recording period is between the minimum set point and the maximum set point (or over the minimum set point), the monitoring module 400 sets the state for the fault code to critical. Such a state may indicate one or more immediate actions are required to address the triggered fault code. For example, the actions may include sending one or more notifications to one or more appropriate parties indicating one or more components and/or sub-systems associated with the fault code are in need of immediate attention such as repair and/or replacement.

Similarly, a set of parameters for a "Caution" state may include a minimum set point (e.g., lower limit) and/or a maximum set point (e.g., upper limit). In this instance, if the monitoring module 400 determines the number of times the fault code was triggered during the recording period is between the minimum set point and the maximum set point (or over the minimum set point), the monitoring module 400 sets the state for the fault code to "caution." In this instance, the caution state may indicate one or more actions are required, but may be viewed as less critical than if the state had been set to critical. For example, the actions for this state may involve sending one or more notifications to one or more appropriate parties that one or more components and/or sub-systems associated with the fault code should be monitored for potential failure.

A set of parameters for an "Environmental" state are related to occurrences of fault codes signaling failure and/or potential failure of one or more components and/or sub-systems of a vehicle 110 that may affect the environment. For example, in some instances, if a vehicle 110 is having antilock brake problems, the vehicle 110 may not go into overdrive in order to attempt to minimize the risk associated with the antilock brake problem. As a result of the vehicle 110 not going into overdrive, the vehicle 110 will typically get less fuel economy (e.g., the vehicle 110 will consume more fuel than if the vehicle 110 were in overdrive). Thus, the consumption of more fuel is considered a direct effect on the environment because of the higher use of more natural resources. Thus, in instances in which the failure or potential failure of one or more components and/or sub-systems associated with a particular fault code may result in an effect on the environment, a set of parameters may be set up to evaluate these instances, Similar to the sets of "Critical" and "Caution" parameters, the set of "Environmental" parameters may include a minimum set point (e.g., lower limit) and/or a maximum set point (e.g., upper limit). For this particular set of parameters, if the monitoring module 400 determines the number of times the fault code was triggered during the recording period is between the minimum set point and the maximum set point (or over the minimum set point), the monitoring module 400 sets the state to "environmental" indicating one or more actions should be taken (e.g., sending one or more notifications to one or more appropriate parties that one or more components and/or sub-systems associated with the fault code may have a problem that affects the environment).

Finally, similar to the sets of parameters already described, the sets of parameters for a "Normal" state and for a "Low Occurrence" state may include a minimum set point (e.g., lower limit) and/or a maximum set point (e.g., upper limit). In various embodiments, the difference between these two sets of parameters is that if the monitoring module 400 determines the number of times the fault code was triggered during the recording period is between the minimum set point and the maximum set point (or over the minimum set point) for the set of parameters for the "Normal" state, the monitoring module 400 sets the state to normal which may trigger such actions as sending one or more notifications to the appropriate parties that the fault code has been triggered however no immediate action is required to address the triggered fault code. In particular embodiments, the "Normal" state may serve to put the one or more parties on notice that the particular fault code was triggered. On the other hand, if the monitoring module 400 determines the number of times the fault code was triggered during the recording period is between the minimum set point and the maximum set point (or over the minimum set point) for the set of parameters for the low occurrence state, the monitoring module 400 sets the state to "low occurrence" indicating no actions need be taken.

As one of ordinary skill the art should understand in light of this disclosure, the above-described sets of parameters are provided as an example of the sets of parameters that may be defined for a particular fault code and should not be construed as the only sets of parameters that may be defined for a particular fault code. In addition, in particular embodiments, the sets of parameters defined for a particular fault code may not be the same sets of parameters defined for other fault codes. For instance, a particular fault code may be associated with one or more components and/or sub-systems of the vehicle 110 that if a problem arises may affect the environment. For this particular fault code, the parameters may include a set of "Environmental" parameters. However, another fault code may not be associated with components and/or sub-systems of the vehicle 110 that if a problem arises may affect the environment. Therefore, the parameters for this particular fault code may not include a set of "Environmental" parameters. Finally, it should be noted that in particular embodiments, the values of parameters may overlap with respect to sets of parameters. For example, a fault code may include an upper limit parameter of one-hundred (100) and a lower limit parameter of fifty (50) for a set of "Caution" parameters and an upper limit parameter of sixty (60) and a lower limit parameter of forty (40) for a set of "Environmental" parameters.

Returning now to FIG. 4, the monitoring module 400 uses the sets of parameters to evaluate the information read for the particular fault code received from the vehicle 110. Thus, in Step 425, the monitoring module 400 determines, based on the set of parameters defined for the "Critical" state, whether the state for the fault code should be set to critical. If the monitoring module 400 determines the state should be set to critical, the monitoring module 400 sets the state to critical and performs one or more actions as required by the "Critical" state, shown as Step 430. For instance, in one embodiment, the monitoring module 400 sends one or more notifications to one or more parties who may be involved in repairing and/or replacing one or more components and/or sub-systems associated with the particular fault code. The notifications may be sent using a number of different mechanisms according to various embodiments, such as electronic mail, text messaging, a phone call, and/or some other type of electronic communication. For example, the monitoring module 400 may send email notifications to personnel performing the repair and/or replacement work, to operations to alert them the vehicle 110 may be unavailable for a time period so that the work may be performed, and to inventory and/or procurement so that needed replacement parts may be secured from inventory or ordered so that the parts are available at the time the work is performed. Further, the monitoring module 400 may perform other actions as required by the critical state such as set up work orders for the work to be performed and/or set up purchase orders to purchase replacement parts.

If the monitoring module 400 determines the state should not be set to critical, the monitoring module 400 determines, based on the set of parameters defined for the "Caution" state, whether the state should be set to caution, shown as Step 455. In Step 460, if the monitoring module 400 determines the state should be set to caution, the monitoring module 400 sets the state to caution and performs one or more actions as required by the "Caution" state. For instance, similar to the "Critical" state, the monitoring module 400 may send one or more notifications to one or more appropriate parties. In this instance, the monitoring module 400 may send a notification to maintenance personnel, for example, putting them on notice of potential failure of one or more components and/or sub-systems associated with the particular fault code and that the one or more components and/or sub-systems should be monitored. In addition, the monitoring module 400 may send a notification to operations putting them on notice of the same. As a result, operations may have the driver of the vehicle 110 monitor the vehicle 110 for possible failure of the one or more components and/or sub-systems.

Further, if the monitoring module 400 determines the state should not be set to caution, the monitoring module 400 determines, based on the set of parameters defined for the "Environmental" state, whether the state for the particular fault code should be set to environmental, shown as Step 465. From this determination, the monitoring module 400 may set the state to environmental and take one or more appropriate actions such as sending one or more notifications with respect to one or more components and/or sub-systems associated with the particular fault code indicating a failure or a potential failure of these components and/or sub-systems may have an environmental effect, shown as Step 470. Similarly, in Step 475, the monitoring module 400 determines, based on the set of parameters defined for the "Normal"-state, whether the state for the particular fault code should be set to normal. In particular embodiments, the actions associated with the "Normal" state may involve sending one or more notifications to certain parties to make the parties aware the fault code has been triggered, although the level at which the fault code has been triggered does not normally equate to an associated component and/or sub-system failure. Thus, from this determination, the monitoring module 400 sets the state to normal and performs the appropriate actions, shown as Step 480.

Once the monitoring module 400 has completed the analysis for the various sets of parameters and states for the particular fault code, the monitoring module 400 determines whether the fault code information received from the vehicle 110 includes information on another fault code triggered during the monitoring period, shown as Step 485. If so, the monitoring module 400 reads the information for the additional fault code and performs the same process for the additional fault code as discussed above. Thus, in various embodiments, the monitoring module 400 determines the state to set for the additional fault code. Once, all of the fault codes listed in the fault code information received from the vehicle 110 have been evaluated, the monitoring module 400 ends the process.

It should be noted that the above-discussed configuration of the monitoring module 400 is not the only configuration contemplated with respect to the claimed invention. As mentioned, particular embodiments of the monitoring module 400 may include additional parameters and, as a result, the monitoring module 400 may perform additional analytical steps to determine states to set for fault codes. For instance, in particular embodiments, the parameters for one or more fault codes may include a set of parameters defining a "consecutive period rule" for the fault code. For example, this particular set of parameters may set a count for the number of times a particular fault code is triggered for each predefined time period (e.g., an hour, a shift, a day) of consecutive time periods. In another example, this particular set of parameters may set a count for the number of times a particular fault code is triggered for each predefined set of distance (e.g., set of miles driven) of consecutive sets of distance. Thus, if the particular number of counts is reached for each time period (or set of distance) over consecutive time periods (or consecutive sets of distance) equal to the count, the fault code may be elevated to a particular state without the number of counts for the fault code actually triggering the parameters for the particular state.

For example, the "Critical" parameters for a particular fault code may be defined with an upper limit of one-hundred (100) counts and a lower limit of fifty (50) counts over a period of twenty-four hours. Consecutive parameters for the particular fault code may be defined as thirty (30) counts per day for three consecutive days. For three consecutive days, the count for this particular fault code for a vehicle 110 reaches thirtyfive (35), thirty-two (32), and forty (40). Therefore, in this instance, although the monitoring module 400 may not have set the state for the fault code to critical for any of the three days, the monitoring module 400 may elevate the state for the fault code to critical based on the consecutive parameters.

In addition, it should be noted that in various embodiments, the monitoring module 400 may be configured to set the state to multiple levels for a fault code triggered over a particular time period. For instance, the monitoring module 400 may be configured so that although the count for a particular fault code may trigger the monitoring module 400 to set the state for the particular fault code to caution, the monitoring module 400 may also be configured to evaluate whether the state should also be set to environmental.

Finally, as noted above, it should be understood that in various embodiments, the actions required for a particular state may involve other actions besides the monitoring module 400 sending notifications to different parties. For instance, in one embodiment, the monitoring module 400 may be configured to query information on available inventory for maintenance parts and if a needed part is available in inventory, secure the part for use in repair of the vehicle 110. Further, the monitoring module 400 may be configured to setup and submit a purchase order for a needed part if the part is not available in inventory. In addition, in particular embodiments, the monitoring module 400 may be configured to setup and submit works orders for needed repairs on vehicles 110 and schedule maintenance personal for performing the needed repairs. One of ordinary skill in the art can envision numerous actions that may be defined for states in light of this disclosure.

b. Interface Module

As previously described, in various embodiments, the monitoring system 180 (e.g., the monitoring server 200) may also include an interface module 500 that provides functionality and screens to allow users to interact with the monitoring system 180. For instance, the interface module 500 in particular embodiments provides a graphical user interface comprising one or more screens that allow users to set up parameters for various fault codes and to monitor fault codes triggered for various vehicles 110. FIGS. 5-8 provide illustrations of different screens and functionality provided by the interface module 500 according to various embodiments.

FIG. 5 provides an illustration of a screen used by individuals to set parameters for a particular fault code (e.g., a flashcode). The screen is broken into two sections, the diagnostic data section 510 and the flashcode data section 515. For this particular screen, the diagnostic data shown in this section 510 is defined by the Society of Automotive Engineers (SAE) or the manufacturer. As shown, the engine type 520 of the vehicle and diagnostics 525 used to address the fault code are identified. For instance, the diagnostics 525 may be the definition of the parameter identifier (PID), subsystem identifier (SID), and/or suspect parameter number (SPN). In particular embodiments, the failure mode 575 is typically a predetermined set of properties that describes the condition of a failure. For instance, the failure mode 575 shown in FIG. 5 is the data is valid but above normal operational range. In some instances, for diesel engines, the fault code may be a combination of the PID/SID/SPN and the failure mode. For gas engines, the fault code may be the failure mode or diagnostic trouble code (DTC).

The flashcode data shown in the flashcode data section 515 of FIG. 5 identifies the parameter values used in analyzing gathered fault data information for the fault code 2639 530. In addition to showing the fault code 2639 530, the section 515 provides a description 535 of the fault code 2639 530 and the location of a help file 540 for the fault code 2639 530. In particular embodiments, an individual may use the screen to type in a "plain English" description of the fault code 2639 530. In addition, in particular embodiments, the screen may also provide a link to the listed help file 540.

Further, in particular embodiments, the screen allows an individual to set and modify parameters for the fault code 530. For example, as shown in FIG. 5, the parameters include minimum and maximum values for the critical-immediate attention parameters 545 (e.g., the "Critical" state), the caution-attention required parameters 550 (e.g., the "Caution" state), the green-environmental issue parameters 555 (e.g., the "Environmental" state), the normal parameters 560 (e.g., the "Normal" state), and the low-hidden from normal view parameters 565 (e.g., the "Low Occurrence" state). In addition, the screen allows an individual to enable "3 Day Rule" parameters 570 for the fault code 530 and to set such parameters. Thus, the screen shown in FIG. 5 facilitates the management of evaluation parameters for a number of fault codes that may be triggered and encountered in fault data information gathered on various vehicles 110.

FIG. 6 provides an illustration of a screen providing a listing of vehicles 110 and fault codes triggered for the vehicles 110 over a date range. As shown in FIG. 6, an individual may select a "From Date" 610 and a "To Date" 615 and the screen provides a listing of vehicles 110 and fault codes triggered on the vehicles 110 during the selected time period. The screen displays a number of different pieces of information for each record provided in the listing. For instance, the screen displays a vehicle number 620 for each record along with a fault code (e.g., flash code) 625 triggered for the vehicle 110. In addition, the screen displays the number of counts 630 the fault code 625 was triggered during the selected time period and the failure code 635. Further, the screen displays additional information such as the failure 640, the failure mode 645, the engine type 650, and the automotive technician 655 responsible for working on the vehicle 110.

In particular embodiments, the vehicle field 620 may also include a folder 660. This folder indicates an individual (e.g., an automotive technician 655) has entered a note regarding the condition associated with the particular fault code record. In these particular embodiments, a user of the screen may select the folder 660 to view the individual's note. In addition, in particular embodiments, the failure field 640 may include a malfunction indicator lamp 665 to signal failure that may require some type of action (e.g., immediate attention). Further, in particular embodiments, the fault codes 625 may be displayed in colors to represent the level of priority associated with each fault code (e.g., the state for each fault code).

FIG. 7 provides a further illustration of a screen providing a listing of triggered fault codes for vehicles 110 and a pop-up screen on which an individual (e.g., an automotive technician 655) can provide a comment for a particular fault code 710 triggered during a particular time period for a particular vehicle 715. In this instance, the pop-up screen displays the failure 720 and the failure mode 725 associated with the fault code 710. Thus, the individual may type in a note in the area provided 730 listing the work performed to address the particular fault code 710. Such information may be helpful in various embodiments in revising and establishing parameters used to analyze fault data received for the particular fault code 710 and revising and establishing instructions provided to address the particular fault code 710.

For instance, a set of parameters may be triggered based on number of counts received for the particular fault code 710 and a notification may have been sent to check for coolant leaks and if no leaks were found, to possibly repair the ECL signal. In this instance, the automotive technician 655 finds no leaks and replaces the ECL sensor instead of repairing the ECL signal. Thus, the technician 655 enters a note on the work performed to remedy the fault code 710 being triggered. Such information may be used to fine tune the instructions sent the next time the same fault code 710 is triggered and a notification is sent. In another instance, the automotive technician 655 may find no leaks or problems with the ECL signal or ECL sensor. Thus, in this instance, the set of parameters may be adjusted so that a notification is only sent after the number of counts reaches a higher value.

Finally, FIG. 8 provides an illustration of a screen in which functionality has been implemented to locate a particular vehicle 110 from the listing of triggered fault codes for vehicles 110. In a particular embodiment, a user may click on a vehicle locator for a particular vehicle 110 from the listing. In turn, a screen is shown that provides a location of the vehicle 110. Typically, such functionality may be provided by utilizing GPS capabilities on the vehicle 110 to provide a location for the vehicle 110. For instance, the screen provided in FIG. 8 is of an overhead photograph that includes an indicator 810 of the vehicle's location. However, as one of ordinary skill in the art can envision, other types of screens and information may be provided to a user to enable the user to location the vehicle 110. For instance, in one embodiment, a screen may be provided that simply provides a written description of the vehicle's location. This description may be provided by the last individual who operated the vehicle or may be derived from GPS readings.

As a result of providing such functionality, an individual, such as an automotive technician 655 or driver, may be able to location the vehicle 110 easily so that maintenance may be performed on the vehicle 110 and/or the vehicle 110 may be located for use after maintenance has been completed on the vehicle 110.

c. Additional Comments

It should be understood that the functionality of various modules and screens described above may be combined or separated in particular embodiments. Therefore, the descriptions of the various modules and screens are provided above as they relate to the functionality performed by various embodiments of the invention and should not be construed to limit the scope of the claimed invention.

VI. CONCLUSION

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

The invention claimed is:

1. A system for managing fault codes associated with a vehicle, the system comprising:
a memory storing a plurality of parameters and a plurality of fault codes, wherein each parameter is associated with a fault code and said plurality of parameters comprise:
an upper limit and a lower limit associated with a particular fault code, the upper limit and lower limit defining a range of a number of times the particular fault code is generated during a predefined time period the vehicle was in operation; and
a threshold value and a consecutive value associated with the particular fault code, the threshold value defining a threshold number of times the particular fault code is generated during the predefined time period the vehicle was in operation and the consecutive value defining a number of consecutive predefined time periods during which the threshold value was met or exceeded; and
one or more computer processors configured to:
receive fault code information retrieved from the vehicle, the fault code information comprising one or more of said plurality of fault codes, the one or more fault codes generated during a particular time period the vehicle was in operation;
retrieve parameters stored in the memory associated with the one or more fault codes;
analyze the fault code information to identify each of the one or more fault codes signaling failure or potential failure of one or more components or sub-systems of the vehicle based at least in part on the parameters associated with the one or more fault codes in the fault code information; and
set a state for each identified fault code, based at least in part on the parameters associated with each identified fault code, the state indicating a level of action associated with the identified fault code, wherein the state for the particular fault code is set by the processors in response to the fault code information showing that the particular fault code was generated a number of times within the range defined by the upper limit and lower limit during the predefined time period, and wherein the state for the particular fault code is also set by the processors in response to the fault code information showing that the particular fault code was generated a number of times meeting or exceeding the threshold value during a number of consecutive time periods meeting or exceeding the consecutive value.

2. The system of claim 1, wherein the state comprises one of a caution state indicating the one or more components or sub-systems of the vehicle should be monitored, a critical state indicating the one or more components or sub-systems of the vehicle should be repaired, or an environmental state indicating the failure or potential failure of the one or more components or sub-systems of the vehicle affects one or more environmental conditions.

3. The system of claim 1, wherein the one or more computer processors are configured to send one or more notifications to one or more parties for each of the identified fault codes, the one or more notifications comprising the state for each of the identified fault codes.

4. The system of claim 1, wherein the one or more computer processors are configured to initiate a work order for repair of at least one of the one or more components or sub-systems of the vehicle.

5. The system of claim 1, further comprising an interface configured to provide access to one or more procedures for diagnosing the one or more components or sub-systems associated with each of the identified fault codes.

6. The system of claim 5, wherein the one or more procedures for diagnosing the one or more components or sub-systems are dependent on manufacturers of the one or more components or sub-systems of the vehicle.

7. The system of claim 5, wherein the interface is further configured to display comments provided by one or more individuals on performing the one or more procedures for diagnosing the one or more components or sub-systems.

8. The system of claim 5, wherein the interface is further configured to provide a map displaying the GPS coordinates of the vehicle.

9. The system of claim 5, wherein the interface is further configured to display results of performing the one or more procedures for diagnosing the one or more components or sub-systems.

10. The system of claim 1, further comprising an interface configured to provide access to one or more maintenance procedures associated with each of the identified fault codes.

11. The system of claim 10, wherein the one or more maintenance procedures are dependent on manufacturers of the one or more components or sub-systems of the vehicle.

12. The system of claim 10, wherein the interface is further configured to display comments provided by one or more individuals on results of performing the one or more maintenance procedures.

13. The system of claim 10, wherein the interface is further configured to display results of performing the one or more maintenance procedures.

14. A method for managing fault codes associated with a vehicle, the method comprising the steps of:
receiving fault code information retrieved from the vehicle, the fault code information comprising one or more fault codes generated during a particular time period the vehicle was in operation;
analyzing the fault code information by one or more computer processors, to identify each fault code from the one or more fault codes signaling failure or potential failure of one or more components or sub-systems of the vehicle based at least in part on a comparison of the fault code information and one or more parameters associated with the one or more fault codes, wherein the one or more parameters comprise:
an upper limit and a lower limit associated with a particular fault code, the upper limit and lower limit defining a range of a number of times the particular fault code is generated during a predefined time period the vehicle was in operation; and
a threshold value and a consecutive value associated with the particular fault code, the threshold value defining a threshold number of times the particular fault code is generated during the predefined time period the vehicle was in operation and the consecutive value defining a number of consecutive predefined time periods during which the threshold value was met or exceeded; and
setting a state for each identified fault code by the one or more computer processors, based at least in part on the parameters associated with each identified fault code, the state indicating a level of action to address the identified fault code, wherein the state for the particular fault code is set by the processors in response to the fault code information showing that the particular fault code was generated a number of times within the range defined by the upper limit and lower limit during the predefined time period, and wherein the state for the particular fault code is also set by the processors in response to the fault code information showing that the particular fault code was generated a number of times meeting or exceeding the threshold value during a number of consecutive time periods meeting or exceeding the consecutive value.

15. The method of claim 14, wherein the state comprises one of a caution state indicating the one or more components or sub-systems of the vehicle should be monitored, a critical state indicating the one or more components or sub-systems of the vehicle should be repaired, or an environmental state indicating the failure or potential failure of the one or more components or sub-systems of the vehicle affects one or more environmental conditions.

16. The method of claim 14, further comprising the step of sending one or more notifications to one or more parties for each of the identified fault codes, the one or more notifications comprising the state for each of the identified fault codes.

17. The method of claim 14, further comprising the step of initiating a work order for repair of at least one of the one or more components or sub-systems of the vehicle.

18. The method of claim 14, further comprising the step of providing access via an interface to one or more procedures for diagnosing the one or more components or sub-systems associated with each of the identified fault codes.

19. The method of claim 18, further comprising the step of displaying comments provided by one or more individuals on performing the one or more procedures for diagnosing the one or more components or sub-systems.

20. The method of claim 18, further comprising the step of displaying results of performing the one or more procedures for diagnosing the one or more components or sub-systems.

21. The method of claim 14, further comprising the step of providing access via an interface to one or more maintenance procedures associated with each of the identified fault codes.

22. The method of claim 21, further comprising the step of displaying comments provided by one or more individuals on results of performing the one or more maintenance procedures.

23. The method of claim 21, further comprising the step of displaying results of performing the one or more maintenance procedures.

24. A non-transitory computer program product comprising executable instructions for managing fault codes associated with a vehicle that when executed by at least one computer processor are configured to cause the at least one computer processor to:
receive fault code information retrieved from the vehicle, the fault code information comprising one or more fault codes generated during a particular time period the vehicle was in operation;
analyze the fault code information based on one or more parameters, the one or more parameters being associated with the one or more fault codes from the fault code information, in order to identify each fault code from the one or more fault codes signaling failure or potential failure of one or more components or sub-systems of the vehicle, wherein the one or more parameters comprise:
an upper limit and a lower limit associated with a particular fault code, the upper limit and lower limit defining a range of a number of times the particular fault code is generated during a predefined time period the vehicle was in operation; and
a threshold value and a consecutive value associated with the particular fault code, the threshold value defining a threshold number of times the particular fault code is generated during the predefined time period the vehicle was in operation and the consecutive value defining a number of consecutive predefined time periods during which the threshold value was met or exceeded; and
set a state for each identified fault code, based at least in part on the parameters associated with each fault code, the state indicating a level of action to address the identified fault code, wherein the state for the particular fault code is set in response to the fault code information showing that the particular fault code was generated a number of times within the range defined by the upper limit and lower limit during the predefined time period, and wherein the state for the particular fault code is also set in response to the fault code information showing that the particular fault code was generated a number of times meeting or exceeding the threshold value during a number of consecutive time periods meeting or exceeding the consecutive value.

* * * * *